(12) United States Patent
Olson

(10) Patent No.: US 8,425,511 B2
(45) Date of Patent: Apr. 23, 2013

(54) CLAMP AND SCISSOR FORCEPS

(75) Inventor: Jessica E. C. Olson, Frederick, CO (US)

(73) Assignee: Covidien LP, Mansfield, MA (US)

( * ) Notice: Subject to any disclaimer, the term of this patent is extended or adjusted under 35 U.S.C. 154(b) by 502 days.

(21) Appl. No.: 12/748,028

(22) Filed: Mar. 26, 2010

(65) Prior Publication Data
US 2011/0238066 A1    Sep. 29, 2011

(51) Int. Cl.
*A61B 18/00* (2006.01)
*A61B 17/28* (2006.01)

(52) U.S. Cl.
USPC ............................. 606/51; 606/206

(58) Field of Classification Search ............... 606/45–52
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 5,254,129 A | 10/1993 | Alexander |
| 5,324,289 A | 6/1994 | Eggers |
| D348,930 S | 7/1994 | Olson |
| 5,352,222 A | 10/1994 | Rydell |
| 5,456,684 A | 10/1995 | Schmidt et al. |
| 5,573,535 A | 11/1996 | Viklund |
| 5,637,111 A * | 6/1997 | Sutcu et al. ............... 606/51 |
| D384,413 S | 9/1997 | Zlock et al. |
| 5,700,261 A | 12/1997 | Brinkerhoff |
| 5,779,701 A | 7/1998 | McBrayer et al. |
| 5,827,281 A | 10/1998 | Levin |
| 5,964,758 A | 10/1999 | Dresden |
| 5,984,938 A | 11/1999 | Yoon |
| D424,694 S | 5/2000 | Tetzlaff et al. |
| D425,201 S | 5/2000 | Tetzlaff et al. |
| 6,179,837 B1 | 1/2001 | Hooven |
| D449,886 S | 10/2001 | Tetzlaff et al. |
| 6,350,264 B1 | 2/2002 | Hooven |
| 6,358,268 B1 | 3/2002 | Hunt et al. |
| D457,958 S | 5/2002 | Dycus et al. |
| D457,959 S | 5/2002 | Tetzlaff et al. |
| 6,425,896 B1 | 7/2002 | Baltschun et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Michael Peffley
*Assistant Examiner* — Amanda Scott

(57) ABSTRACT

A forceps includes a housing having a shaft attached thereto and an end effector assembly disposed at a distal end of the shaft, the end effector assembly includes first and second jaw members disposed in opposed relation relative to one another. At least one of the jaw members is moveable relative to the other between a spaced-apart position and an approximated position for grasping tissue therebetween. Each of the jaw members includes first and second longitudinal jaw halves. At least one of the first and second jaw halves of each jaw member is moveable with respect to the other jaw half between an aligned position and a displaced position for cutting tissue disposed between the jaw members.

5 Claims, 4 Drawing Sheets

U.S. PATENT DOCUMENTS

| | | | |
|---|---|---|---|
| 6,464,701 B1 | 10/2002 | Hooven et al. | |
| 6,520,960 B2 * | 2/2003 | Blocher et al. | 606/51 |
| D493,888 S | 8/2004 | Reschke | |
| 6,773,434 B2 | 8/2004 | Ciarrocca | |
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,470,276 B2 * | 12/2008 | Tu | 606/144 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 2004/0078035 A1 | 4/2004 | Kanehira et al. | |
| 2008/0319442 A1 | 12/2008 | Unger et al. | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 7/2001 |
| DE | 10045375 | 10/2002 |
| DE | 10 2004 026179 | 12/2005 |
| DE | 20 2007 009317 | 10/2007 |
| DE | 19738457 | 1/2009 |
| EP | 0913126 | 5/1999 |
| EP | 1159926 | 12/2001 |
| EP | 1330991 | 7/2003 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO0059392 | 10/2000 |
| WO | WO 01/54604 | 8/2001 |
| WO | WO0166025 | 9/2001 |
| WO | WO 2005/110264 | 11/2005 |

OTHER PUBLICATIONS

U.S. Appl. No. 09/591,328, filed Jun. 9, 2000.
U.S. Appl. No. 10/246,087, filed Sep. 17, 2002.
U.S. Appl. No. 12/336,970, filed Dec. 17, 2008.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/665,081, filed Dec. 17, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/762,482, filed Apr. 19, 2010.
U.S. Appl. No. 12/766,476, filed Apr. 23, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/820,024, filed Jun. 23, 2010.
U.S. Appl. No. 12/821,253, filed Jun. 23, 2010.
U.S. Appl. No. 12/832,772, filed Jul. 8, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With The LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.

Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11159771 dated Jun. 30, 2011.

* cited by examiner

CLAMP AND SCISSOR FORCEPS

BACKGROUND

The present disclosure relates to surgical instruments. More particularly, the present disclosure relates to surgical forceps and methods for clamping, sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a forceps including a housing having a shaft attached thereto and an end effector assembly disposed at a distal end of the shaft. The end effector assembly includes first and second jaw members disposed in opposed relation relative to one another. One or both of the jaw members is moveable relative to the other between a spaced-apart position and an approximated position for grasping tissue therebetween. Each jaw member includes first and second longitudinal jaw halves. One or both of the jaw halves of each jaw member is moveable with respect to the other jaw half between an aligned position and a displaced position for cutting tissue disposed between the jaw members.

In one embodiment, the first jaw halves of each jaw member and the second jaw halves of each of the jaw members cooperate to move in unison upon movement of the jaw halves between the aligned and displaced positions for shear-cutting tissue disposed between the jaw members.

In another embodiment, the first and second jaw halves of each jaw member are fixed in the aligned position during movement of the first and second jaw members between the spaced-apart position and the approximated position.

In yet another embodiment, the first and second jaw members are fixed in the approximated position during movement of the first and second jaw halves of each of the jaw members between the aligned position and the displaced position.

In still another embodiment, an opposed surface of the first and second jaw halves of each jaw member defines a shearing surface for shear-cutting tissue upon movement of the jaw halves between the aligned position and the displaced position.

In yet another embodiment, one or both of the jaw members includes an electrically conductive tissue sealing surface disposed on a tissue-facing surface thereof. The electrically conductive tissue sealing surface(s) includes first and second sealing surface sections disposed on each of the first and second jaw halves of the jaw member. One or both of the sealing surface sections is adapted to connect to a source of electrosurgical energy for sealing tissue disposed between the jaw members.

In still yet another embodiment, the forceps includes a locking mechanism for locking the jaw members in the approximated position and/or for locking the jaw halves of each of the jaw members in the aligned position.

In another embodiment, the forceps includes a handle assembly coupled to the housing. The handle assembly is configured to move the jaw members between the spaced-apart position and the approximated position.

In yet another embodiment, the forceps includes a trigger mechanism disposed on the housing. The trigger mechanism is configured for moving the jaw halves between the aligned position and the displaced position.

In accordance with another embodiment of the present disclosure, an end effector assembly for use with a surgical instrument is provided. The end effector assembly includes first, second, third and fourth jaw quadrant members. Each jaw quadrant member includes a tissue sealing surface and a shearing surface. The tissue sealing surfaces of the first and third jaw quadrant members oppose one another and the tissue sealing surfaces of the second and fourth jaw quadrant members oppose one another. The shearing surfaces of the first and second jaw quadrant members oppose one another, while the shearing surfaces of the third and fourth jaw quadrant members oppose one another. The jaw quadrant members are moveable in each of a grasping mode and a cutting mode. During movement in the grasping mode, the first and second jaw quadrant members move in unison with one another and the third and fourth jaw quadrant members move in unison with one another relative to and in an opposite direction with respect to the first and second jaw quadrant members for grasping tissue between the sealing surfaces of the jaw quadrant members. During movement in the cutting mode, the first and third jaw quadrant members move in unison with one another and the second and fourth jaw quadrant members move in unison with one another relative to and in an opposite direction with respect to the first and third jaw quadrant members for shear-cutting tissue with the shearing surfaces of the jaw quadrant members.

The present disclosure also relates to a method of grasping and cutting tissue. The method includes the steps of providing a forceps according to any of the above embodiments. The method further includes positioning the jaw members such that tissue to be cut is disposed between the jaw members, moving the jaw members to the approximated position to grasp tissue therebetween, and moving the jaw halves to the displaced position to cut tissue grasped between the jaw members.

In one embodiment, the method includes fixing the first and second jaw halves of each jaw member in the aligned position during movement of the first and second jaw members to the approximated position.

In another embodiment, the method includes fixing the first and second jaw members in the approximated position during movement of the first and second jaw halves of each jaw member to the displaced position.

In yet another embodiment, the method also includes supplying electrosurgical energy to one (or more) of the sealing surface sections for sealing tissue grasped between the jaw members.

BRIEF DESCRIPTION OF THE DRAWINGS

Various embodiments of the presently disclosed forceps are described herein with reference to the drawings, wherein.

DETAILED DESCRIPTION

Figure 1:
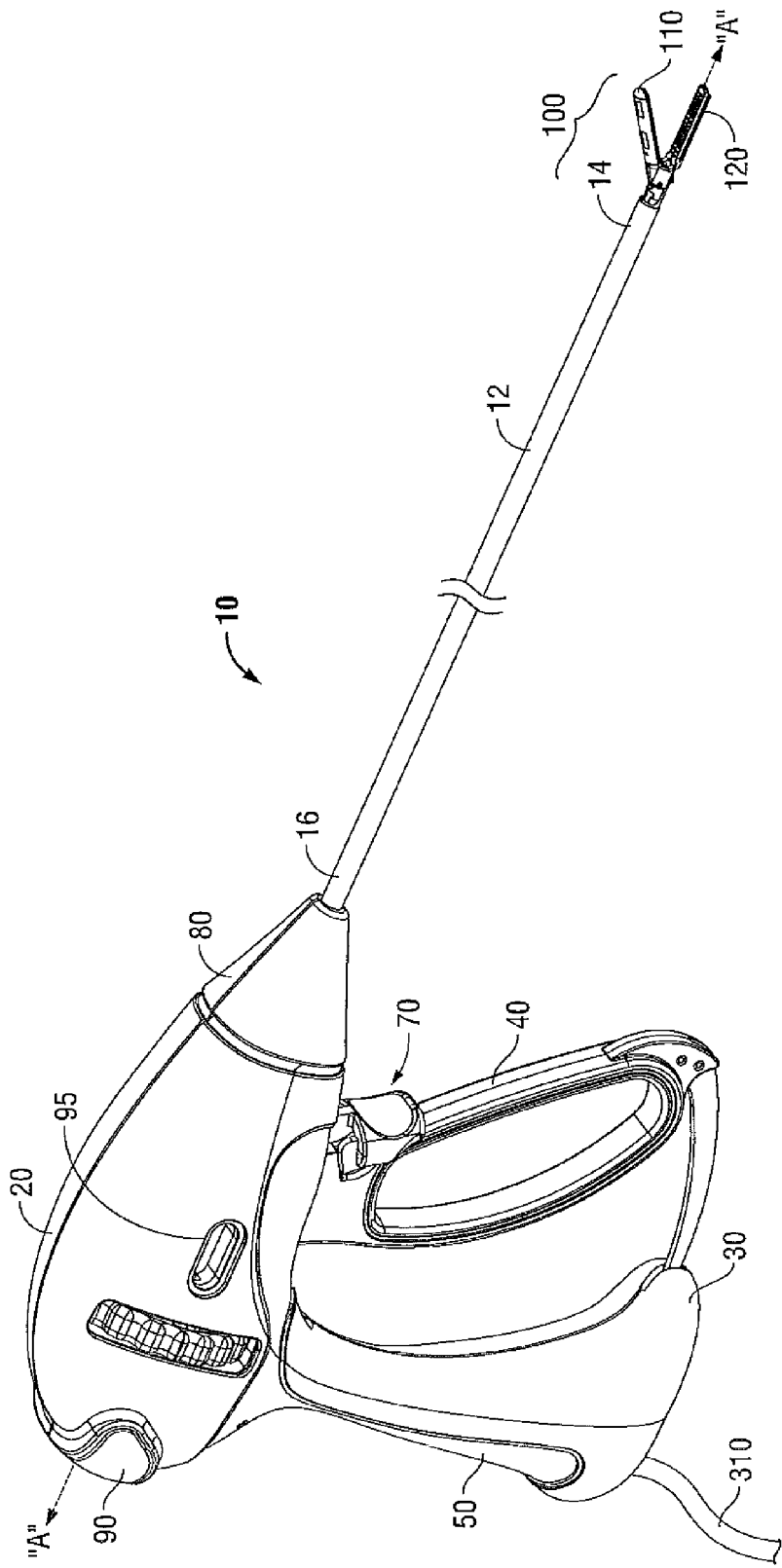
FIG. 1 is a perspective view of a forceps including an end effector assembly in accordance with the present disclosure.

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIG. 1, a forceps 10 is provided including a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. Housing 20 includes two halves that form a cavity dimensioned to house the internal working components of forceps 10. Housing 20 also includes a control switch 90 and a lock switch 95 disposed thereon.

Figure 2:
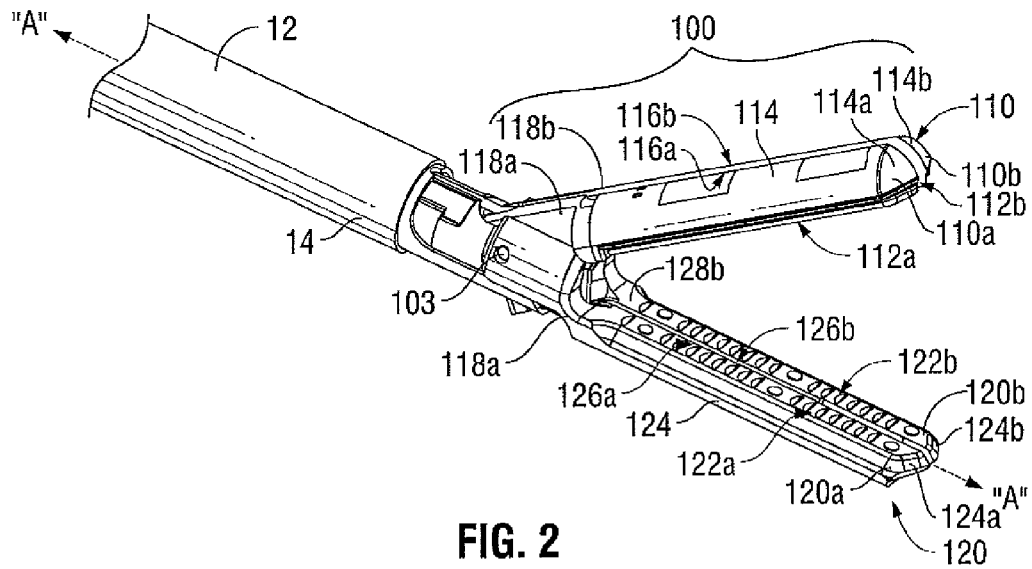
FIG. 2 is an enlarged, perspective view of the end effector assembly of the forceps of FIG. 1.

End effector assembly 100 includes a pair of opposed jaw members 110 and 120 made up of first and second longitudinal jaw halves 110a, 110b and 120a, 120b, respectively (see FIG. 2). In other words, end effector assembly 100 includes four jaw quadrant members 110a, 110b, 120a and 120b. End effector assembly 100 is designed as a unilateral assembly, i.e., jaw member 120 is fixed relative to shaft 12 and jaw member 110 is moveable about a pivot 103 (FIG. 2) relative to jaw member 120. However, either, or both jaw members 110, 120 may be moveable with respect to the other. First longitudinal jaw halves 110a, 120a (FIG. 2) and second longitudinal jaw halves 110b, 120b (FIG. 2) of jaw members 110, 120, respectively, are also moveable with respect to one another and may be configured for unilateral or bilateral movement.

Forceps 10 further includes an electrosurgical cable 310 that connects forceps 10 to a generator (not shown). Cable 310 has sufficient length to extend through shaft 12 in order to provide electrical energy to at least one of jaw members 110 and 120 of end effector assembly 100. Alternatively, forceps 10 may be battery-operated, thus including a battery assembly (not shown) disposed within housing 20 for providing electrical energy to the jaw member(s) 110, 120. Control switch 90 is disposed on housing 20 and is coupled to cable 310 (or the battery assembly (not shown)) for controlling, e.g., activating/deactivating, the supply of electrosurgical energy to jaw member 110 and/or jaw member 120.

Rotating assembly 80 is integrally associated with housing 20 and is rotatable approximately 180 degrees in either direction about a longitudinal axis "A-A" to rotate end effector assembly 100 with respect to housing 20 about longitudinal axis "A-A."

With continued reference to FIG. 1, handle assembly 30 includes a fixed handle 50 and a moveable handle 40. Fixed handle 50 is integrally associated with housing 20 and moveable handle 40 is moveable relative to fixed handle 50. Moveable handle 40 of handle assembly 30 is ultimately connected to a first drive assembly (not shown) that, together, mechanically cooperate to impart movement of jaw members 110 and 120 between an open, or spaced-apart position and a closed, or approximated position. Trigger 70 is positioned on housing 20 and is selectively actuatable, e.g., depressible. Trigger 70 is operably-connected to a second drive assembly (not shown), that, together, mechanically cooperate to impart movement of jaw members halves 110a and 120a (FIG. 2) with respect to jaw member halves 110b and 120b (FIG. 2) between an aligned position (see FIG. 3) and a displaced position (see FIG. 5).

FIG. 2 shows jaw members 110, 120 disposed in the spaced-apart position. As shown in FIG. 2, longitudinal jaw halves 110a and 110b are disposed in the aligned position wherein sealing surface sections 112a, 112b of jaw halves 110a, 110b, respectively, form a generally planar sealing surface 112 extending across a tissue-facing surface of jaw member 110 and wherein outer jaw housing sections 114a, 114b of jaw halves 110a, 110b, respectively, cooperate to form the hemi-cylindrical outer jaw housing 114 of jaw member 110. In other words, when jaw member halves 110a, 110b are in the aligned position, the complete jaw member 110, as shown in FIG. 2, is formed. Similarly, when longitudinal jaw halves 120a, 120b of jaw member 120 are disposed in the aligned position, sealing surface sections 122a, 122b form a generally planar sealing surface 112 extending across a tissue-facing surface of jaw member 120 and outer jaw housing sections 124a, 124b of jaw member 120 cooperate to form the hemi-cylindrical outer jaw housing 124 of jaw member 120. Thus, the complete jaw member 120 is formed when jaw member halves 120a, 120b are disposed in the aligned position.

Figure 4A:
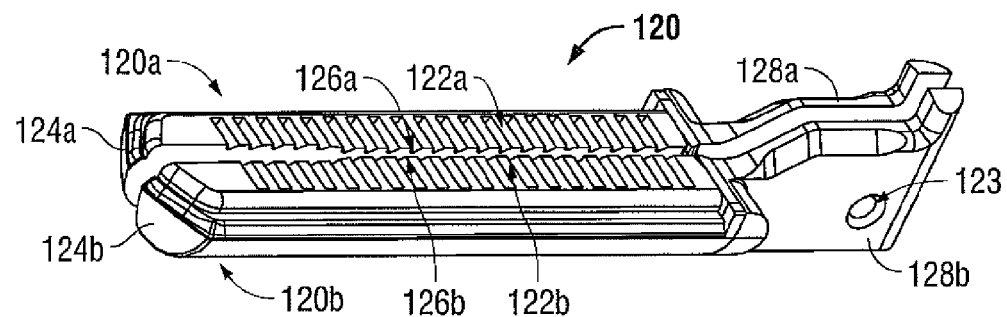
FIG. 4A is a perspective view of the second jaw member of the end effector assembly of the forceps of FIG. 1.
Figure 4B:
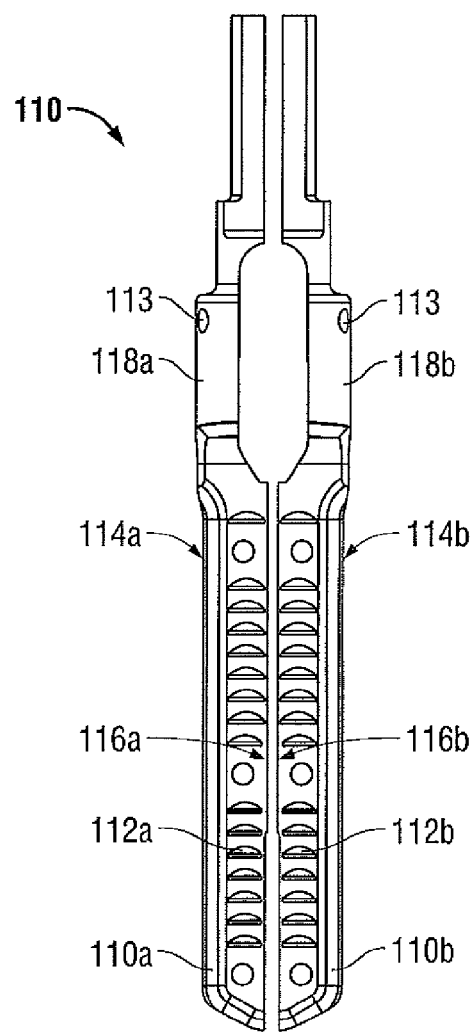
FIG. 4B is a bottom view of the first jaw member of the end effector assembly of the forceps of FIG. 1.

As shown in FIG. 4B, jaw quadrants, or jaw halves 110a, 110b of jaw member 110 include opposing surfaces 116a, 116b. Opposing surfaces 116a, 116b of jaw halves 110a, 110b, respectively, may be configured as shearing surfaces 116a, 116b. Similarly, as shown in FIG. 4A, jaw quadrants, or jaw halves 120a, 120b of jaw member 120 include opposing shearing surface 126a, 126b. When jaw halves 110a, 110b and 120a, 120b of respective jaw members 110, 120 are in the aligned position, as shown in FIGS. 4B and 4A, respectively, shearing surfaces 116a, 116b of jaw member 110 are positioned adjacent to and aligned with one another and, similarly, shearing surfaces 126a, 126b of jaw member 120 are positioned adjacent to and aligned with one another.

With continued reference to FIGS. 4A and 4B, each jaw half 110a, 110b, 120a, 120b includes a proximal flange 118a, 118b, 128a, 128b, respectively, extending proximally from respective jaw halves, 110a, 110b, 120a, 120b. An aperture 113 is defined within each of proximal flanges 118a, 118b of respective jaw halves 110a, 110b of jaw member 110. Apertures 113 are aligned with one another and cooperate with the first drive assembly (not shown) to permit jaw member halves 110a, 110b to pivot with respect to jaw member 120 and also cooperate with the second drive assembly (not shown) to permit jaw member halves 110a, 110b to pivot with respect to one another. Similarly, an aperture 123 cooperating with each of the first and second drive assemblies (not shown) is defined within each of proximal flanges 128a, 128b of respective jaw halves 120a, 120b of jaw member 120 to permit pivoting of jaw member halves 120a, 120b with respect to jaw member 110 (via the first drive assembly (not shown)) and with respect to one another (via the second drive assembly (not shown)).

Referring back to FIG. 1, in conjunction with FIGS. 4A and 4B, lock switch 95 is disposed on housing 20 and may be operably-coupled to end effector assembly 100 for locking jaw members halves 110a, 110b with respect to each other and for locking jaw member halves 120a, 120b with respect to each other in the aligned position (and/or the displaced position). Lock switch 95 may be selectively depressible to lock jaw members halves 110a, 110b, 120a, 120b in the aligned position (and/or the displaced position) and may include mechanical or electro-mechanical components. More particularly, lock switch 95 may cooperate with the second drive assembly (not shown) for fixing the relative position of proximal flanges 118a and 118b of jaw member 110 to maintain the aligned position of jaw halves 110a, 110b of jaw members 110. Similarly and simultaneously, upon depression of lock switch 95, the relative position of proximal flanges 128a, 128b of jaw member 120 may be fixed to maintain jaw halves 120a, 120b of jaw member 120 in the aligned position. Additionally, jaw member halves 110a, 110b and 120a, 120b of jaw members 110 and 120, respectively, may be biased, e.g., via a spring (not shown), toward the aligned position. In such an embodiment, lock switch 95 may be utilized to prevent inadvertent displacement of the jaw halves 110a, 110b and 120a, 120b of respective jaw members 110, 120 from the aligned position, for example, as a result of inadvertent actuation of trigger 70 (FIG. 1).

Jaw member halves 110a, 110b, 120a, 120b may be configured to automatically lock in the aligned position upon movement of moveable handle 40 with respect to fixed handle 50 and/or may be configured to lock when jaw members 110, 120 are moved to the spaced-apart position. In other words, end effector assembly 100 may be configured such that jaw member halves 110a, 110b, 120a, 120b are inhibited from being displaced from the aligned position, i.e., jaw member halves 110a, 110b, 120a, 120b are locked in the aligned position, when jaw members 110, 120 are not disposed in the approximated position (see FIG. 3). Locking jaw member halves 110a, 110b, 120a, 120b in the aligned position permits jaw member halves 110a, 110b, 120a, 120b to move in unison as jaw members 110 and 120 are moved between the spaced-apart and approximated positions for grasping tissue between sealing surfaces 112, 122 of jaw members 110, 120, respectively.

Jaw members 110, 120 may also be configured to lock in the approximated position when jaw member halves 110a, 110b, 120a, 120b are in the displaced position. Accordingly, end effector assembly 100 may be configured such that, when jaw members 110, 120 are moved between the approximated position and the spaced-apart position (or when jaw members 110, 120 are disposed in the spaced-apart position), jaw member halves 110a, 110b, 120a, 120b are fixed in the aligned position and such that, when jaw member halves 110a, 110b, 120a, 120b are moved between the aligned position and the displaced position (or when jaw members halves 110a, 110b, 120a, 120b are disposed in the displaced position), jaw members 110, 120 are fixed in the approximated position. In other words, end effector assembly 100 may be configured to operate in two mutually exclusive modes: a grasping mode and a shearing, or cutting mode. In the grasping mode, jaw member halves 110a, 110b move in unison with one another and jaw member halves 120a, 120b move in unison with one another in an opposite direction with respect to jaw member halves 110a, 110b to grasp tissue between the completely formed sealing surfaces 112, 122 of jaw members 110, 120, respectively. In the cutting mode, jaw member halves 110a, 120a move in unison with one another and jaw member halves 110b, 120b move in unison with one another in an opposite direction with respect to jaw member halves 110a, 120a to cut tissue between shearing surfaces 116a, 116b, and 126a, 126b of jaw members 110, 120, respectively.

As mentioned above, trigger 70 (FIG. 1) may be coupled to the second drive assembly (not shown) for moving jaw member halves 110a, 110b, 120a, 120b between the aligned and displaced positions. The second drive assembly (not shown) may be coupled to a spring assembly (not shown) for urging jaw member halves 110a, 110b, 120a, 120b from the aligned position to the displaced position. As mentioned above, jaw member halves 110a, 110b, 120a, 120b may be biased toward the aligned position such that jaw member halves 110a, 110b, 120a, 120b are returned to the aligned position after being moved, e.g., by the spring biased second drive assembly (not shown) coupled to the trigger 70 (FIG. 1), to the displaced position. Further, trigger 70 (FIG. 1) may be configured to control the actuation, or may be configured to control the positioning of jaw member halves 110a, 110b, 120a, 120b. In other words, trigger 70 (FIG. 1) may be configured such that, upon actuation of trigger 70 (FIG. 1), jaw member halves 110a, 110b, 120a, 120b are urged, e.g., via the spring-biased second drive assembly (not shown), to the displaced position and such that, once the actuation force, e.g., the spring force, dissipates, jaw member halves 110a, 110b, 120a, 120b are returned under the bias toward the aligned position. Alternatively, or additionally, trigger 70 (FIG. 1) may be configured such that, upon depression of trigger 70 (FIG. 1), jaw member halves 110a, 110b, 120a, 120b are urged to the displaced position and, if trigger 70 is maintained in the actuated position, jaw member halves 110a, 110b, 120a, 120b are maintained in the displaced position, only returning to the aligned position under the bias when trigger 70 (FIG. 1) is released from the actuated position.

The operation of forceps 10 is described with reference to FIGS. 1-6. As mentioned above, forceps 10 is configured for use in both a grasping/sealing mode and in a scissoring/shearing mode. Accordingly, forceps 10 provides a single instrument capable of grasping, sealing and/or cutting tissue.

Figure 3:
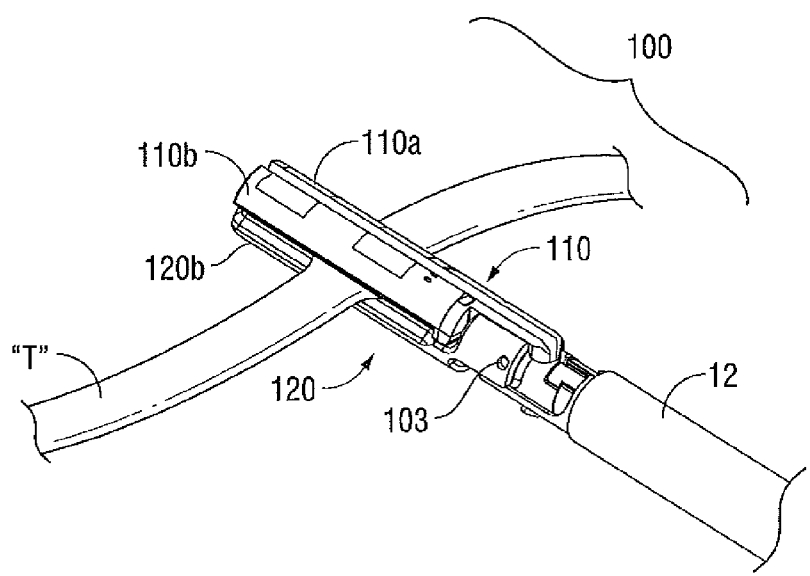
FIG. 3 is an enlarged, perspective view of the end effector assembly of the forceps of FIG. 1 shown grasping tissue between first and second jaw members thereof.

Initially, with respect to the grasping/sealing mode, jaw members 110, 120 of end effector assembly 100 of forceps 10 are disposed in the spaced-apart position and the respective jaw halves 110a, 110b and 120a, 120b of jaw members 110 and 120, respectively, are disposed (or locked) in the aligned position, as shown in FIG. 2. From this position, end effector assembly 100 may be positioned such that tissue to be grasped and/or sealed is disposed between sealing surfaces 112, 122 of jaw members 110, 120, respectively. Next, upon actuation, e.g., upon squeezing moveable handle 40 with respect to fixed handle 50, jaw members 110, 120 are moved to the approximated position to grasp tissue "T" between sealing surfaces 112, 122 of jaw members 110, 120, respectively, as shown in FIG. 3. In this approximated position, wherein tissue "T" is grasped between jaw members 110, 120, jaw halves 110a, 110b, 120a, 120b remain disposed (or locked) in the aligned position. With tissue "T" grasped between sealing surfaces 112, 122, electrosurgical energy may be supplied through cable 310 to sealing surface 112 and/or sealing surface 122, e.g., via activating switch 90 (FIG. 1), to seal tissue disposed between jaw members 110, 120.

Figure 5:
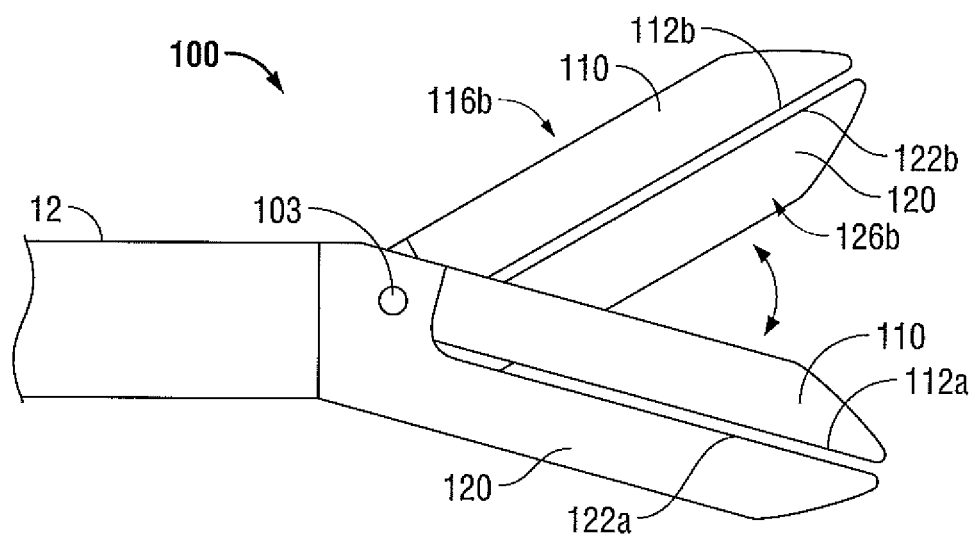
FIG. 5 is a schematic side view of the end effector assembly of the forceps of FIG. 1 showing the first and second jaw halves of each of the jaw members in a displaced position.
Figure 6:
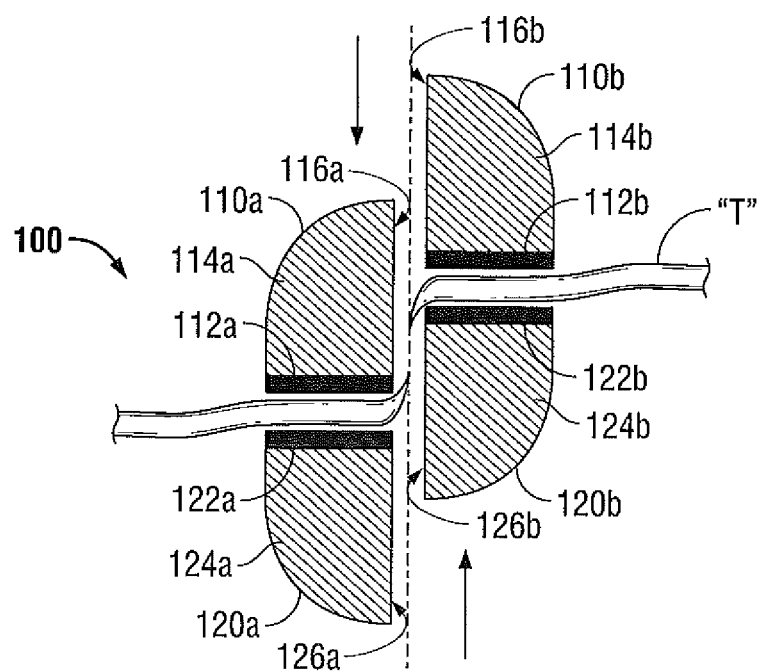
FIG. 6 is a schematic front, cross-sectional view of the end effector assembly of the forceps of FIG. 1 showing the first and second jaw halves of each of the jaw members moving between an aligned position and the displaced position.

With reference to FIGS. 5 and 6, regarding the scissoring/shearing mode, end effector assembly 100 may be used to shear-cut tissue grasped between sealing surfaces 112, 122 of jaw members 110, 120, respectively, e.g., to divide previously sealed tissue "T," and/or may be used to scissor cut tissue disposed between jaw member halves 110a, 120a and 110b, 120b.

To shear-cut tissue, with jaw members 110, 120 disposed in the approximated position, grasping tissue "T," e.g., the previously sealed tissue "T," between respective sealing surfaces 112, 122 thereof, jaw member halves 110a and 120a may be moved with respect to jaw member halves 110b, 120b from the aligned position (FIG. 3) to the displaced position (FIGS. 5 and 6). Alternatively, jaw member halves 110b, 120b may be moved with respect to jaw member halves 110a, 120a, or both sets of jaw member halves 110a, 120a and 110b, 120b may be moveable with respect to each other from the aligned position (FIG. 3) to the displaced position (FIGS. 5 and 6).

In either configuration, trigger 70 (FIG. 1) may be actuated, e.g., depressed, to move jaw member halves 110a, 120a and jaw members halves 110b, 120b with respect to one another from the aligned position to the displaced position. More particularly, as shown in FIGS. 5 and 6, upon depression of trigger 70 (FIG. 1), the second drive assembly (not shown) imparts movement of jaw member halves 110a, 120a in a downward direction with respect to jaw member halves 110b, 120b and/or imparts movement of jaw member halves 110b, 120b in an upward direction with respect to jaw member halves 110a, 120a. As jaw member halves 110a and 110b are moved with respect to one another, opposing shear surface 116a of jaw half 110a slides, or shears with respect opposing shear surface 116b of jaw half 110b initially, as jaw member halves 110a, 110b are moved in opposite directions with respect to one another, and eventually slides, or shears with respect to opposing shear surface 126b of jaw half 120b as jaw halves 110a, 120a are moved further in an opposite direction with respect to jaw member halves 110b, 120b, such that tissue "T" grasped between jaw members 110, 120 is sheared, or divided, as best shown in FIG. 6. Similarly and simultaneously, shearing surface 126a of jaw half 120a initially shears with respect to shearing surface 126b of jaw half 120b, and, upon further movement, shears with respect to shearing surface 116b of jaw half 110b, as jaw member halves 110a, 120a are moved further with respect to jaw member halves 110b, 120b toward the displaced position. Likewise, shearing 116b of jaw half 110b initially shears with respect to shearing surface 116a and eventually with respect to shearing surface 126a, and shearing surface 126b of jaw half 120b initially shears with respect to shearing surface 126a and eventually with respect to shearing surface 116a. The shearing surfaces 116a, 116b, 126a, 126b cut, or tear tissue "T" grasped between jaw members 110, 120 upon movement from the aligned position to the approximated position.

The scissor-cutting operation is similar to the shear-cutting operation except that, instead of jaw member halves 110a, 110b, 120a, 120b moving from the aligned position to the displaced position to cut tissue disposed between the sealing surfaces 112, 122 of jaw members 110, 120, respectively, jaw member halves 110a, 110b, 120a, 120b are returned to the aligned position from the displaced position to cut tissue disposed between the jaw member halves 110a, 120a and jaw member halves 110b, 120b.

For scissor-cutting tissue, jaw members 110, 120 are moved (and fixed) to the approximated position (without tissue grasped therebetween) such that jaw member halves 110a, 110b, 120a, 110b may be moved from the aligned position to the displaced position, e.g., such that jaw member halves 110a, 110b, 120a, 120b are unlocked from the aligned position. Next, as shown in FIG. 5, jaw member halves 110a, 120a may be moved with respect to jaw member halves 110b, 120b (or visa versa) from the aligned position to the displaced position by depressing trigger 70 (FIG. 1) while jaw members 110, 120 remain fixed in the approximated position. Once moved to the displaced position, jaw member halves 110a, 110b, 120a, 120b are retained in the displaced position, e.g., by maintaining trigger 70 (FIG. 1) in the depressed position (as mentioned above) or by any other suitable mechanism.

With jaw members 110, 120 fixed in the approximated position and with jaw member halves 110a, 120a displaced from jaw member halves 110b, 120b, i.e., retained in the displaced position, as shown in FIG. 5, end effector assembly 100 may be positioned such that tissue to be scissor-cut is disposed between the displaced pairs of jaw halves 110a, 120a and 110b, 120b. Jaw member halves 110a, 120a (and/or jaw member halves 110b, 120b) may then be returned to the aligned position with respect to jaw member halves 110b, 120b (and/or jaw member halves 110a, 120a), e.g., by releasing trigger 70 (FIG. 1). More particularly, as jaw member halves 110a, 120a and jaw member halves 110b, 120b are returned to the aligned position, shearing surface 126b of jaw member half 120b and shearing surface 116a of jaw member half 110a eventually slide along, or shear with respect to one another as jaw member halves 110a and 120b are moved in opposite directions relative to one another, e.g., as jaw member halves 110a, 120b are moved toward the aligned position. Accordingly, tissue disposed between shearing surfaces 116a and 126b of jaw member halves 110a, 120b, respectively, is cut, or divided as the two surfaces 116a, 126b are sheared with respect to one another. Upon further movement of jaw member halves 110a, 110b, 120a, 120b toward the aligned position, shearing surfaces 116a and 126b of jaw member halves 110a, 120b, respectively, move past one another, eventually sliding, or shearing with respect to respective shearing surfaces 116b and 126a of jaw halves 110b, 120a to cut tissue that has not yet been divided. In other words, in the scissor-cutting mode, when jaw member halves 110a, 110b, 120a, 120b are moved from the displaced position to the aligned position, jaw member halves 110a and 120a move in unison with one another, acting as a first scissor blade of end effector assembly 100, while jaw member halves 110b and 120b move in unison with one another, acting as a second scissor blade of end effector assembly 100 for scissor-cutting tissue disposed therebetween.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An end effector assembly for use with a surgical instrument, the end effector assembly including:
   first, second, third and fourth elongated jaw quadrant members, each jaw quadrant member including a tissue sealing surface and a shearing surface, the tissue sealing surfaces of the first and third jaw quadrant members opposing one another, the tissue sealing surfaces of the second and fourth jaw quadrant members opposing one another, the shearing surfaces of the first and second jaw quadrant members opposing one another, and the shearing surfaces of the third and fourth jaw quadrant members opposing one another; and
   wherein the jaw quadrant members are moveable in each of a grasping mode and a cutting mode, the first and second jaw quadrant members moving in unison with one another and the third and fourth jaw quadrant members moving in unison with one another relative to and in an opposite direction with respect to the first and second jaw quadrant members during the grasping mode for grasping tissue between the sealing surfaces of the jaw quadrant members, the first and third jaw quadrant members moving in unison with one another and the second and fourth jaw quadrant members moving in unison with one another relative to and in an opposite direction with respect to the first and third jaw quadrant members during the cutting motion for shear-cutting tissue disposed between the shearing surfaces of the jaw quadrant members.

2. The end effector assembly of claim 1, wherein during grasping mode the first and second jaw quadrant members are moveable with respect to the third and fourth jaw quadrant members between a spaced-apart position and an approximated position.

3. The end effector assembly of claim 2, further comprising a locking mechanism for at least one of locking the jaw quadrant members in the approximated position and locking the jaw quadrant members in the grasping mode.

4. The end effector assembly of claim 2, further comprising a handle assembly coupled to a housing and configured for moving the jaw quadrant members between the spaced-apart position and the approximated position.

5. The end effector assembly of claim 4, further comprising a trigger mechanism disposed on the housing and configured for moving the jaw quadrant members during the cutting mode.

* * * * *